United States Patent [19]
Morejohn et al.

[11] Patent Number: 6,042,563
[45] Date of Patent: Mar. 28, 2000

[54] METHODS AND APPARATUS FOR OCCLUDING A BLOOD VESSEL

[75] Inventors: Dwight P. Morejohn, Davis; Ivan Sepetka, Los Altos; Son M. Gia, San Jose, all of Calif.

[73] Assignee: Cardiothoracic Systems, Inc., Cupertino, Calif.

[21] Appl. No.: 09/049,463

[22] Filed: Mar. 27, 1998

[51] Int. Cl.[7] .......................... A61M 29/00; A61M 5/178; A61M 5/00

[52] U.S. Cl. ........................... 604/96; 604/509; 604/164; 604/175; 604/264; 606/194

[58] Field of Search .............................. 604/96, 500, 509, 604/158, 164, 174, 175, 178, 264, 912; 606/192, 194, 158, 191, 195; 128/898

[56] References Cited

U.S. PATENT DOCUMENTS

| | | | |
|---|---|---|---|
| 3,833,003 | 9/1974 | Taricco | 128/347 |
| 4,802,479 | 2/1989 | Haber et al. | 128/344 |
| 5,053,008 | 10/1991 | Bajaj | 604/104 |
| 5,330,451 | 7/1994 | Gabbay | 604/284 |
| 5,425,708 | 6/1995 | Nasu | 604/96 |
| 5,556,412 | 9/1996 | Hill | 606/194 |
| 5,618,307 | 4/1997 | Donlon et al. | 606/205 |
| 5,653,690 | 8/1997 | Booth et al. | 604/96 |
| 5,833,671 | 11/1998 | Macoviak et al. | 604/247 |
| 5,860,997 | 1/1999 | Bonutti | 606/190 |
| 5,934,103 | 8/1999 | Hill . | |

OTHER PUBLICATIONS

Rationale for an extra–vascular aortic clamp, G. Champsaur, M.D., France.

*Primary Examiner*—Ronald Stright
*Assistant Examiner*—Michael J. Hayes
*Attorney, Agent, or Firm*—Lyon & Lyon LLP

[57] ABSTRACT

An improved method and apparatus for occluding a blood vessel is shown and described. A cannula adapted for insertion through a wall of a blood vessel is provided with an expandable member on a distal end which when expanded, substantially fills a cross-sectional annular area of the lumen of the blood vessel. An external clamp is coupled to the cannula and aligned with the expandable member, such that when the clamp is engaged, it moves the annular region of the blood vessel into contact with the inflatable member, the inflatable member and clamp thereby working in cooperation to occlude the blood vessel. The cannula may further be provided with a plurality of lumens extending through the cannula to corresponding openings in a distal end of the cannula, thereby allowing the perfusion of different fluids into the lumen of the blood vessel, both upstream and downstream of the internal occluding member, as well as the venting of fluid from the lumen of the blood vessel. A suture tourniquet may also be coupled to the cannula. Multiple functions are therefore performed by a compact, efficient device that is simple to use. In addition, occlusion is achieved with minimal deformation to the blood vessel, reducing the risk of trauma to the blood vessel and the creation of emboli. The intraluminal occlusion device is also securely held in a selected position, thereby reducing risk of harm to the patient from emboli and undesirable blocking of perfusion of blood to the rest of the patient's body.

16 Claims, 11 Drawing Sheets

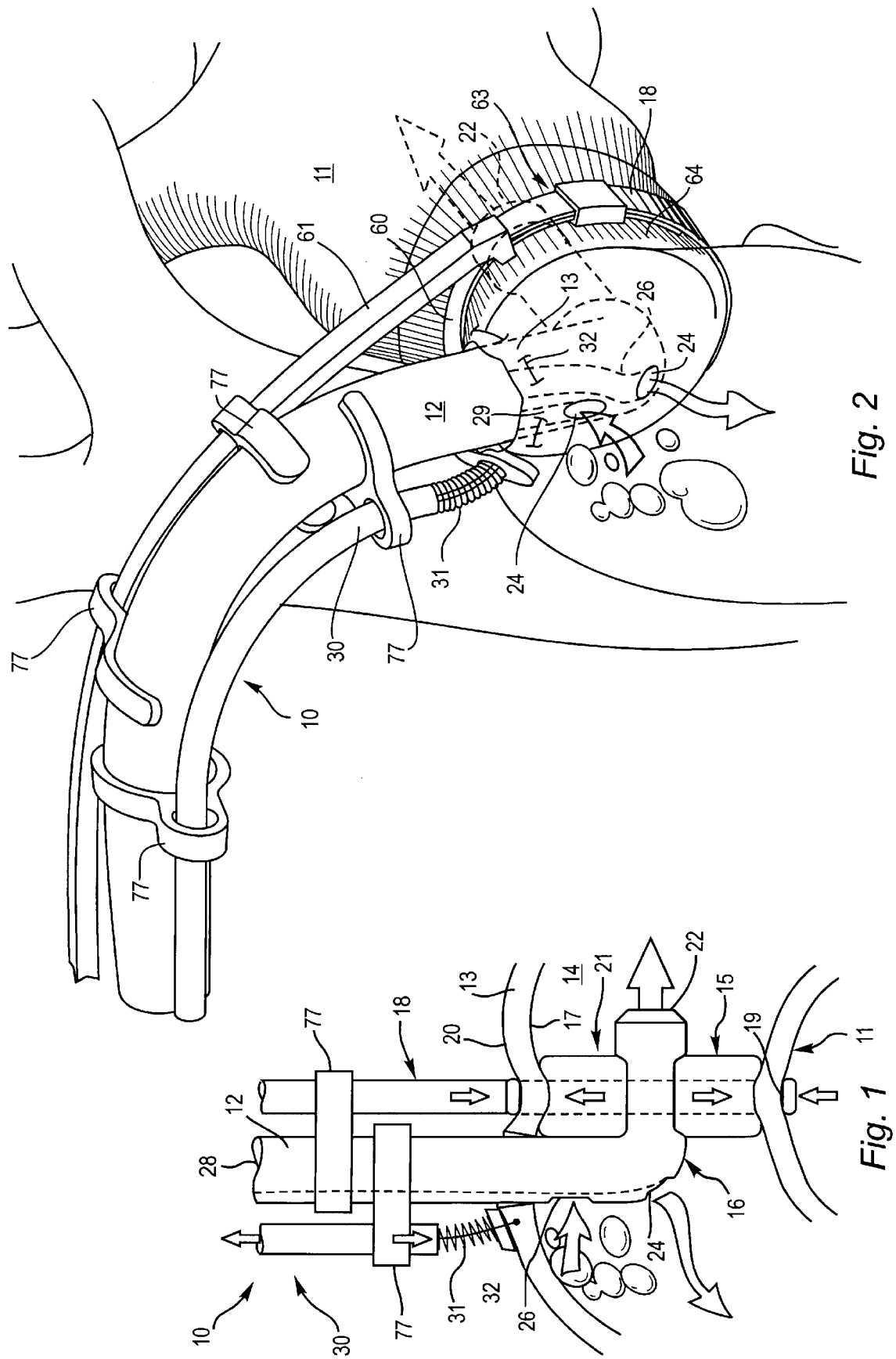

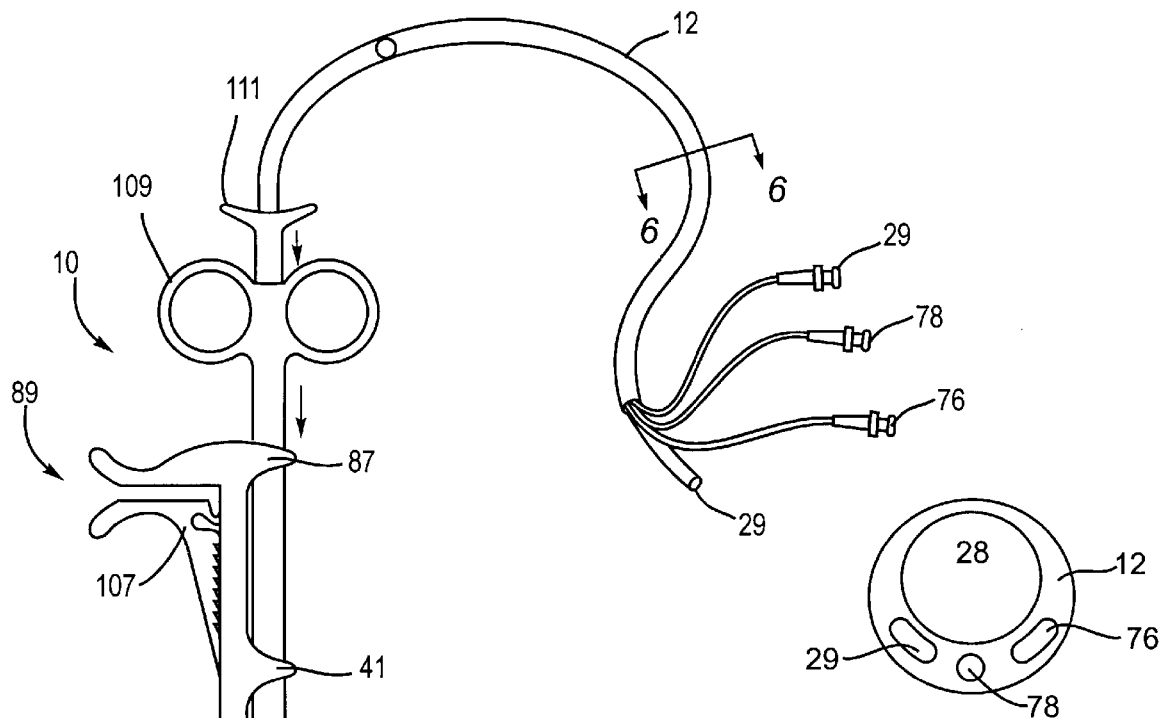
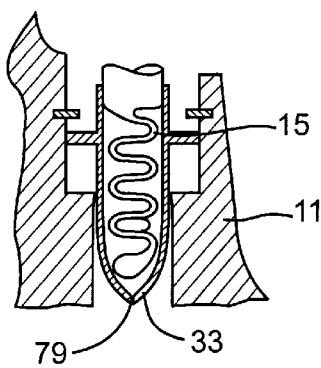
Fig. 6
Fig. 7
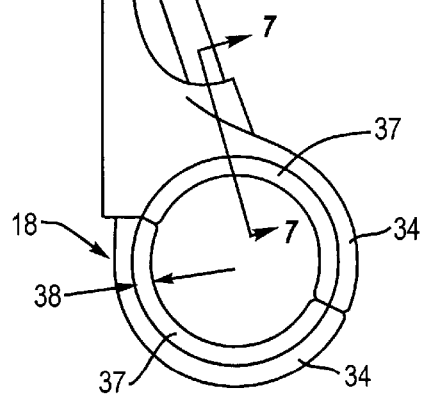
FIG. 5
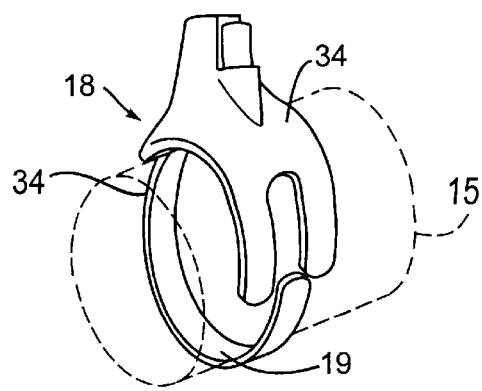
Fig. 4

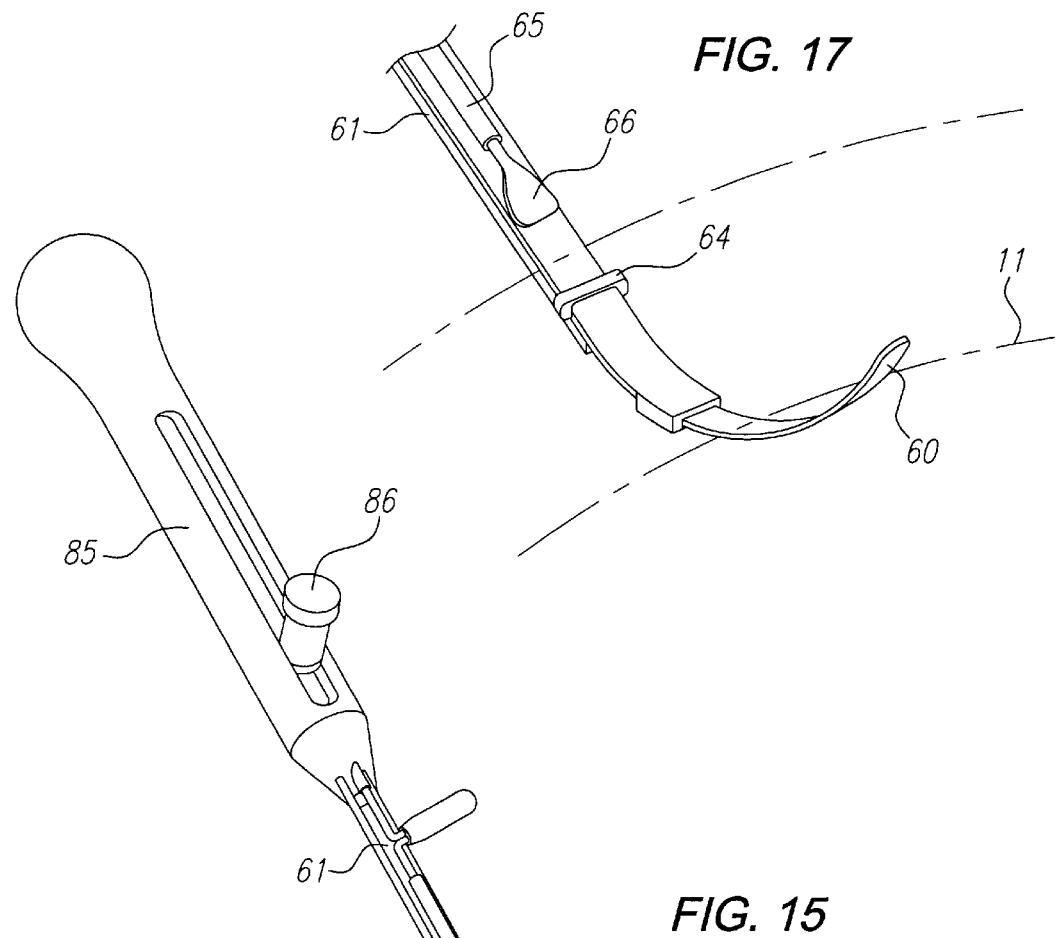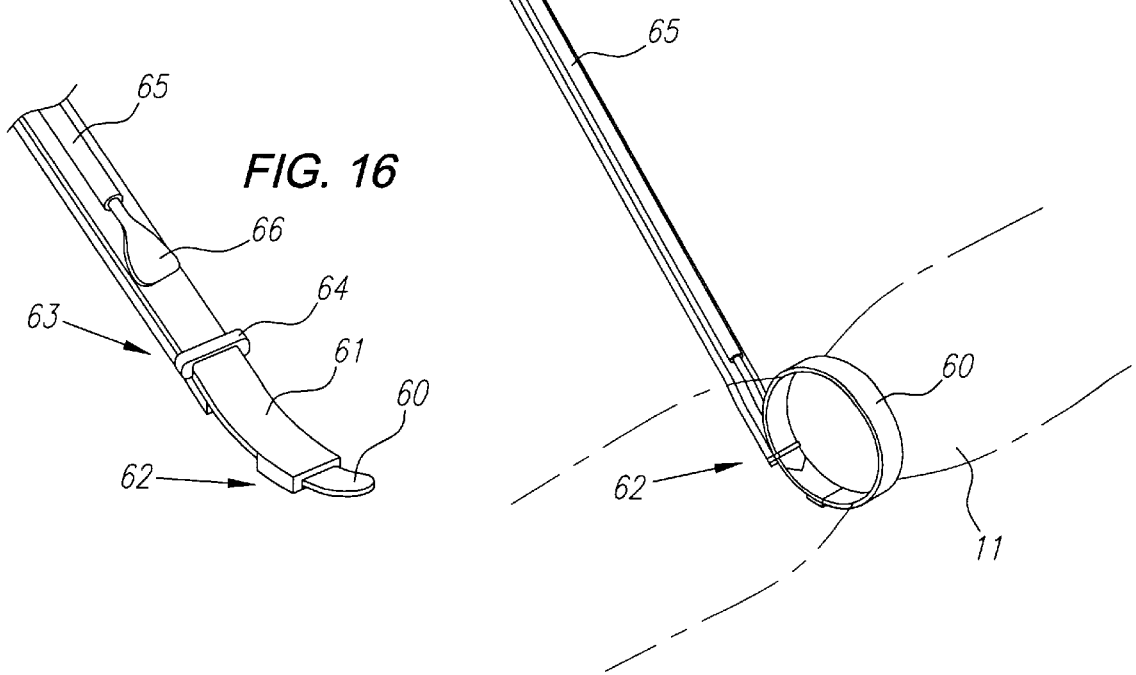

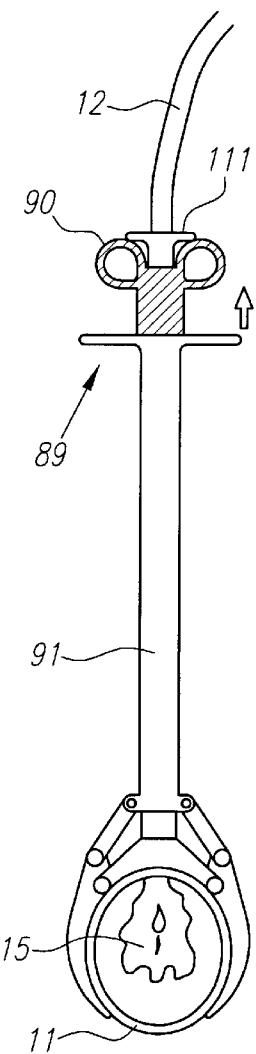
FIG. 26E
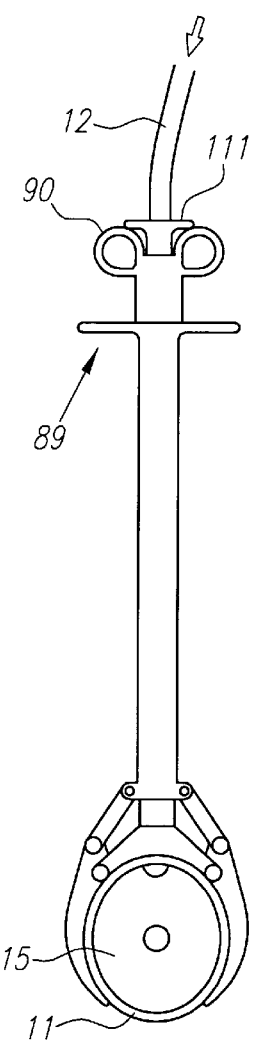
FIG. 26F
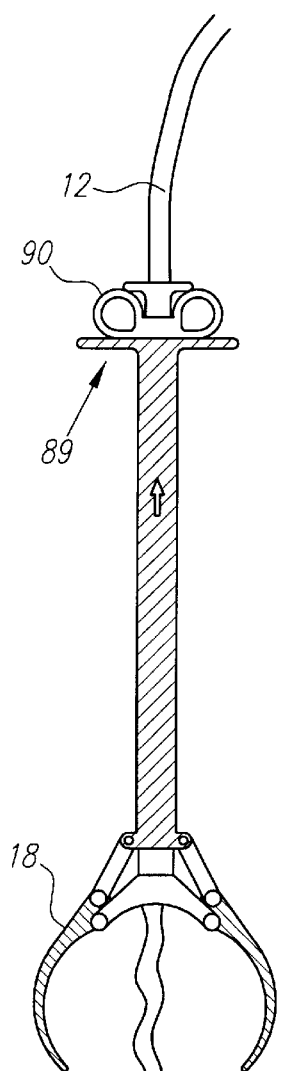
FIG. 26H
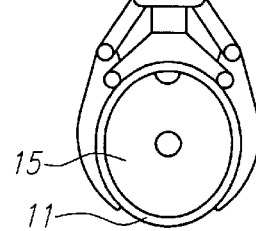
FIG. 26G
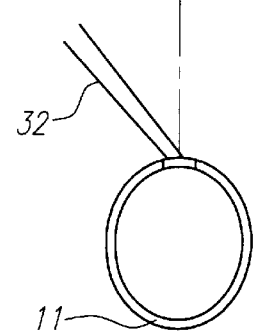

METHODS AND APPARATUS FOR OCCLUDING A BLOOD VESSEL

FIELD OF THE INVENTION

The present invention relates generally to methods and apparatus for occluding a blood vessel, for example the aorta during cardiac surgical procedures, and more particularly, to systems for occluding a blood vessel with minimal trauma to the vessel and to the patient being treated.

BACKGROUND

During various surgical procedures, it is often necessary or desirable to occlude a blood vessel. Once such procedure is cardiopulmonary bypass (CPB) which is commonly used during a variety of cardiac surgical procedures. The essential goals of CPB for heart surgery are to provide life-support functions, a motionless, decompressed heart, and a dry, bloodless field of view for the surgeon. In a basic CPB system, oxygen-poor blood is drained by means of gravity or is siphoned from the patient's venous circulation and is transported to a pump-oxygenator, commonly know as a heart-lung machine, where the blood is exposed to a gaseous mixture that eliminates carbon dioxide and adds oxygen to the blood. The oxygenated blood is then returned or perfused into the patient's arterial circulation for distribution throughout the entire body. This process requires a venous drainage cannula (or cannulae) to be placed into the right side of the heart (typically the right atrium), or directly into the major veins, (e.g. the superior vena cava (SVC) and/or inferior vena cava (IVC), or through peripheral vein access sites (e.g. the femoral vein), to drain unoxygenated blood from the patient and deliver it to the heart-lung machine. Similarly, an arterial or aortic perfusion cannula is placed in the aorta or another large peripheral artery (e.g. the subclavian or common femoral artery), to return or perfuse oxygenated blood to the patient. The heart and lungs of the patient may thereby be effectively bypassed, thus allowing the surgeon to operate on a bloodless heart.

The insertion of the arterial (aortic) perfusion cannula is usually performed in the following fashion. After the patient's chest has been opened and the pericardium (the protective sac around the heart) has been entered, two concentric purse-string sutures are placed in the anterior wall of the ascending aorta just upstream of the brachiocephalic trunk. A "choker" tube or sleeve is positioned over the trailing ends of the suture threads to act as a tourniquet for tightening each of the purse-string sutures. A small incision centered within the purse-string sutures is then made through the wall of the aorta into its lumen. The aortic perfusion cannula is quickly inserted through that incision into the aorta, taking care to minimize the escape of blood from the puncture site. The purse-string sutures are then tightened by means of their respective tourniquets to seal the aortic wall around the perfusion cannula in order to prevent the escape of blood from the aorta. Air is evacuated from the perfusion cannula as it is joined by a connector to tubing from the pump-oxygenator. A cross-clamp is placed on the aorta just downstream of the aortic root and upstream of the perfusion cannula to ensure that no blood flows back into the aorta during CPB.

The venous drainage cannula(e) may be inserted in a similar manner directly through an incision in the right atrium of the heart or into the superior and/or inferior vena cava for connection to the drainage side of the pump-oxygenator.

Once the requisite cannulae are in place and the connections are made to the heart-lung machine, CPB is instituted by allowing unoxygenated blood returning to the right side of the heart to be diverted through the venous drainage cannula(e) into the pump-oxygenator where it is oxygenated and temperature-adjusted. From there, the blood is pumped into the patient's arterial system via the arterial or aortic perfusion cannula to provide oxygen-rich blood to the patient's body and brain.

After CPB has been established, a process known as cardioplegia, which literally means "heart stop," is typically used to arrest the beating of the heart, and in some procedures, to provide oxygen to the myocardium. Cardioplegia is administered by delivering a cardioplegic solution, such as potassium, magnesium or procaine, or a hypocalcemic solution, to the myocardium by one or a combination of two generally known techniques, antegrade and retrograde perfusion.

The antegrade administration of cardioplegia involves the infusion of fluid through the coronary arteries in the normal direction of blood flow. This antegrade flow may be accomplished with a single cardioplegia catheter or a cannula having a distally extending needle obturator. The needle is inserted into the aorta upstream of the aortic clamp and cardioplegic solution is injected into the aortic root and drains in the normal direction of blood flow into the coronary ostia, through the coronary arteries, and into capillaries within the myocardium.

Cardioplegic arrest and CPB are commonly employed during cardiac surgery for treating coronary artery disease and heart valve disease, among other cardiac diseases including atrial and ventricular septal defects. In coronary artery disease, a buildup of stenotic plaque in the coronary arteries causes the arterial lumen to narrow or become completely occluded, restricting or cutting off the blood flow to the heart muscle, which may ultimately result in a myocardial infarction, commonly known as a heart attack. Heart valve disease includes two major categories, namely valvular stenosis, which is an obstruction to forward blood flow through the heart valve, and regurgitation, which is the retrograde leakage of blood through the heart valve. Most commonly, valvular stenosis occurs in the aortic valve while regurgitation is typically a congenital condition affecting the mitral valve.

The major surgical intervention of coronary artery disease is coronary artery bypass grafting (CABG). In this procedure, while the patient is under general anesthesia, a median sternotomy or major thoracotomy is made, the patient is placed on full CPB, and the heart is placed under cardioplegic arrest. Similarly, when it is necessary to repair or replace a malfunctioning heart valve within a patient, the procedure is accomplished through a median sternotomy (typically for an aortic valve procedure) or major thoracotomy (typically for a mitral valve procedure), requiring general anesthesia and total CPB with cardioplegic arrest.

While conventional CABG and valve procedures generally have high efficacy, they are highly traumatic and have significant complications associated with median sternotomy or major thoracotomy, resulting in a prolonged, painful, and expensive recovery. Such conventional procedures also tend to be complicated by the presence of a large number of instruments, sutures, clamps and cannulae, in addition to the relatively large size of the cannulae for CPB and cardioplegic arrest, which potentially inhibit access to the heart, making access via an invasive incision (sternotomy or thoracotomy) unavoidable.

Less invasive surgical techniques and instrumentation have evolved for performing CABG which eliminate the need for a median sternotomy or major thoracotomy, as well as the need to stop the heart and place the patient on CPB. A small incision, such as a mini-thoracotomy or mini-sternotomy, is made in the patient's thoracic cavity and spread open. Specialized retractors are used for accessing arterial conduits, such as the internal mammary arteries, and specialized instruments are used to stabilize the motion of the beating heart while the anastomosis is being established. Although these less invasive surgical procedures have been highly successful, having patency rates as high as conventional CABG procedures and greatly reducing the physical trauma to the patient, a less skilled surgeon doing a highly complex case may still need to place the patient on CPB and stop the heart. As for valve repair and replacement procedures, a less-invasive, beating-heart approach has yet to be perfected.

Also, endoscopic methods and instruments have been developed for performing CABG as well as for performing heart valve repair and replacement. In such procedures, an endoscope and the surgical instruments are introduced and manipulated within the patient's body through small percutaneous incisions or puncture sites. The entire surgical procedure can then be viewed by the surgeon through the endoscope. With such procedures, the cannulae and catheters for establishing CPB and cardioplegic arrest are also introduced percutaneously or via a cut-down in a peripheral vessel and then endovascularly advanced into the patient's vasculature to the desired site.

Most commonly in such endovascular procedures, arterial perfusion of blood is accomplished via cannulation of the femoral artery with the retrograde delivery of an aortic occlusion balloon to the ascending aorta. However, this method of perfusion is associated with a high incidence of complications, such as dissection of the aorta and migration of the occlusion balloon. More particularly, when the balloon is inflated to occlude the aorta, the wall of the aorta is often deformed radially outward to ensure a substantial seal. Such deformation of the wall of the aorta, especially during inflation, may dislodge embolic material such as plaque from the wall of the aorta, which may then flow downstream, for example to the brain, thereby harming the patient. Further, because the wall of the aorta may be distorted substantially when the balloon is inflated, particularly if the balloon is excessively inflated, the wall of the aorta may be damaged or may even rupture.

Occlusion balloons may also "walk" or drift within the aorta because of the substantial pressure of the blood being delivered through the arterial cannula and/or the pumping of the heart prior to cardioplegic arrest. If the inflated balloon travels downstream, it may at least partially occlude the brachiocephalic trunk, thereby reducing and/or preventing blood delivery to the brain or elsewhere, which may again cause great harm to the patient.

Alternatively, oxygenated blood may be returned to the patient's arterial system by use of "central" cannulation, wherein a perfusion cannula is placed directly into the ascending aorta through a puncture in the aortic wall.

As discussed previously, when central cannulation is used during a cardiac surgical procedure, a cross clamp is typically used to occlude the aorta. Such clamps typically include a pair of jaws that engage an outer surface of the aorta and compress opposing sides of the vessel wall together until the vessel's lumen is squeezed shut. Oxygenated blood is delivered into the ascending aorta distal or downstream of the clamp, for example using an arterial cannula as discussed above. With the clamp in place, oxygenated blood perfuses the patient's body in a substantially normal direction, and is prevented from traveling proximally or upstream into the heart. In addition, cardioplegic solution may be delivered proximal or upstream of the clamp into the aortic root. The cardioplegic solution is thereby directed into the coronary ostia in an antegrade manner, and not into the patient's arterial system.

Conventional clamps, however, have many risks associated with their use. For example, as mentioned above, patients undergoing cardiac surgery often have a substantial build-up of plaque on the interior wall of the aorta which may be brittle. The engagement and release of the clamp may break-off and dislodge pieces of the plaque from the wall of the aorta, creating emboli which in turn can cause severe harm to the patient, such as a stroke.

In addition, the pressure applied by a clamp and the resulting deformation of the aorta may damage the wall of the aorta itself. Further, a clamp applied to the outer wall of the aorta may damage connective tissues or nerves, for example those extending between the aorta and the pulmonary arteries.

Therefore, there is a need for an improved system for occluding a blood vessel during surgery, for example the aorta during cardiac surgery, that minimizes the risk of harm to the patient and/or that facilitates minimally invasive surgical procedures.

The present invention fulfills these needs, and provides further related advantages, as will become apparent from the following description and accompanying drawings of the invention, taken in conjunction with the appended claims.

SUMMARY OF THE INVENTION

Briefly, the present invention provides an improved apparatus and method for occluding a blood vessel as part of a surgical procedure, for example, occluding the aorta during cardiopulmonary bypass. In a preferred embodiment, a cannula is provided which is adapted to be inserted through a wall of a blood vessel such that a distal end of the cannula is positioned within the lumen of the blood vessel. An expandable member is coupled to a distal end of the cannula, the expandable member having a sufficient size when expanded to be adjacent an inner surface of the blood vessel. A clamp is coupled to the cannula, the clamp having an inner surface that is configured to engage an outer surface of the annular region of the blood vessel. The clamp and expandable member are aligned with each other, such that the clamp moves the annular region of the blood vessel into contact with the expandable member. As such, the expandable member and the clamp work in cooperation to occlude the blood vessel and maintain the expandable member in a desired location. A variety of external clamps and intraluminal occlusion devices may be used in accordance with the present invention.

The cannula may further be provided with a plurality of lumens extending through the cannula and in fluid communication with a plurality of openings in a distal end of the cannula. The lumens allow perfusion of different fluids into the lumen of the blood vessel, both upstream and downstream of the intraluminal occlusion device, as well as the venting of fluid from the lumen of the blood vessel. A suture tourniquet may also be coupled to the cannula.

Multiple functions are therefore performed by a compact, efficient device that is simple to use. In addition, occlusion is achieved with minimal deformation to the blood vessel, reducing the risk of trauma to the blood vessel and the creation of emboli. The intraluminal occlusion device is also securely held in a selected position, thereby reducing risk of harm to the patient from emboli and undesirable blocking of perfusion of blood to the rest of the patient's body.

BRIEF DESCRIPTION OF THE DRAWINGS

FIG. 1 is a partial cross-sectional elevational view of an apparatus for occluding a blood vessel provided in accordance with the present invention.

FIG. 2 is an isometric view of the apparatus of FIG. 1 shown in use in an aorta.

FIG. 4 is a front isometric view of a portion of the apparatus illustrated in FIG. 5.

FIG. 5 is a side elevational view of an apparatus for occluding a blood vessel provided in accordance with the present invention.

FIG. 6 is a cross-sectional elevational view taken along line 6—6 of FIG. 5.

FIG. 7 is a cross-sectional elevational view of a portion of the apparatus illustrated in FIG. 5.

FIG. 15 is an isometric view of an apparatus to occlude a blood vessel provided in accordance with the present invention.

FIG. 16 is an enlarged partial view of the apparatus of FIG. 15.

FIG. 17 is an isometric view of the apparatus of FIG. 16 illustrated in use surrounding a blood vessel.

FIGS. 26A–H are front elevational views of an apparatus for occluding a blood vessel provided in accordance with the present invention shown in various stages of use.

DETAILED DESCRIPTION OF THE INVENTION

Figure 3:
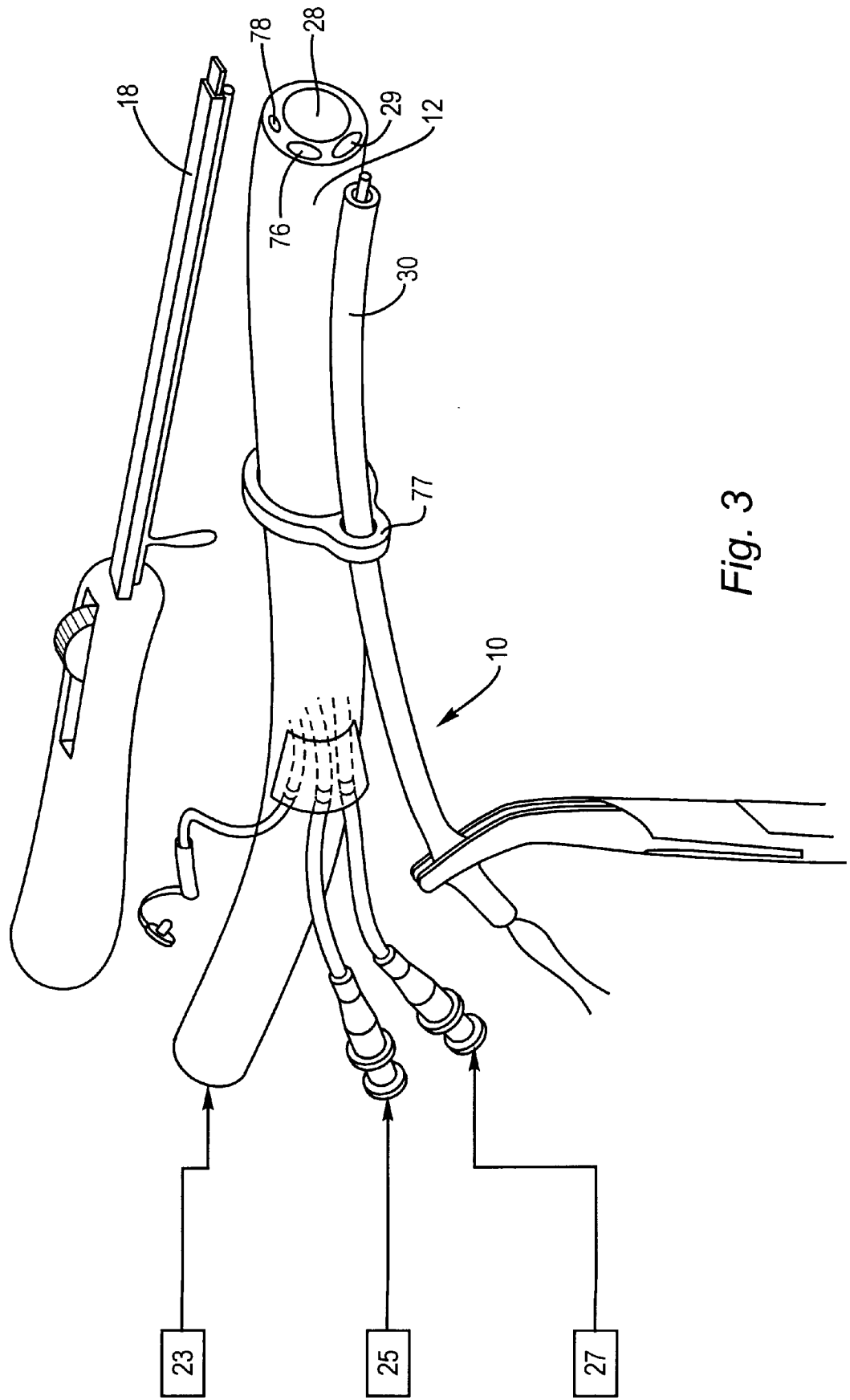
FIG. 3 is a partial sectional isometric view of the apparatus of FIG. 1.

An improved apparatus 10 for occluding a blood vessel is provided in accordance with the present invention. In a first preferred embodiment, as illustrated in FIGS. 1 and 2, the apparatus 10 includes a cannula 12 adapted to be inserted through a wall 13 of a blood vessel 11, such that a distal end 16 of the cannula 12 is positioned within a lumen 14 of the blood vessel 11. (For purposes of illustration, the various embodiments of the present invention are shown in use in a patient's aorta. It should be understood, however, that the application of the devices and methods disclosed herein is not limited to use in the aorta.) An intraluminal occlusion device comprising an expandable member 15 is coupled to the distal end 16 of cannula 12. When in its extended condition, the expandable member 15 is of sufficient size to be adjacent an inner surface 17 of blood vessel 11. A clamp 18 is coupled to the cannula 12. An inner surface 19 of the clamp 18 engages an outer surface 20 of the blood vessel 11 in an annular region 21 that is aligned with the expandable member 15. As such, when the clamp 18 engages the annular region 21 of the blood vessel 11, it moves the annular region 21 into contact with the expandable member 15, the clamp 18 and expandable member 15 thereby working in cooperation to occlude the blood vessel.

A preferred embodiment of clamp 18 is shown in FIG. 1 cooperating with the expandable member 15 to occlude the vessel. The clamp 18 comprises a shaft 61 having a band 60 that is slidably disposed along and past a distal end 62 of the shaft 61. The band 60 is sufficiently pliable and preshaped to form a loop around the blood vessel 11 as the distal end of the band 60 is moved past the distal end of the shaft 61. The band 60 is looped around the vessel 11 until the distal end of the device comes in locking engagement with a locking member 63. The locking member comprises a bracket 64 having a sufficient width to receive the distal end of the band 60.

Clamp 18 further serves to maintain the expandable member 15 in a desired position. As a result, precise and secure placement of the intraluminal occlusion device is achieved, given the cooperation of the clamp and expandable member, and the spatial relationship of the clamp 18, expandable member 15 and cannula 12. Furthermore, the walls of the blood vessel 11 do not need to be highly distorted either by the clamp 18 or the expandable member 15 to occlude the vessel, as is required in conventional systems. The risk of emboli and harm to the patient is thereby reduced. Further, because occlusion is not achieved by the expandable member 15 alone or by the clamp 18 alone, but rather by the interaction of the clamp 18 and the expandable member 15 on opposite sides of the blood vessel wall, the expandable member 15 is not over-expanded, thereby reducing the risk of rupturing the expandable member 15 and/or the blood vessel. Moreover, any under expansion of expandable member 15 may be compensated for by the compression of clamp 18 on the vessel wall.

As further illustrated in FIGS. 1–3, the distal end 16 of the cannula 12 is provided with a first opening 22 in fluid communication with a perfusion lumen 28, a second opening 24 in fluid communication with a cardioplegia lumen 76, and a third opening 26 in fluid communication with a venting lumen 29. As best seen in FIG. 3, the perfusion, venting, and inflation lumens extend through the length of the cannula 12, and in a preferred embodiment, are integrally formed therein. The lumens therefore allow fluid flow through the cannula 12 into and out of the lumen 14 of the blood vessel 11. For example, the perfusion lumen 28 may be coupled to a source of oxygenated blood 23 thereby allowing blood to be perfused into the blood vessel downstream of the occlusion. The cardioplegia lumen 76 may be coupled to a source of cardioplegia 25 thereby allowing perfusion of cardioplegia upstream of the occlusion. The venting lumen 29 may be coupled to a vacuum source 27, such that the third opening 26 and venting lumen 29 act as a vent for the lumen 14 of the blood vessel 11. As further illustrated in FIG. 3, a balloon inflation lumen 78 may be provided in the cannula 12 in fluid communication with the expandable member 15 to allow the inflation of the expandable member by the introduction of liquid, gas or foam through the cannula.

As further illustrated in FIGS. 1 and 2, a suture tourniquet 30 is coupled to the cannula 12, the suture tourniquet 30 including a spring 31 which engages the suture 32 to place and maintain the suture 32 in tension. Although the suture tourniquet 30, cannula 12 and clamp 18 may be coupled together in a variety of ways, in a preferred embodiment, clips 77 are provided to grasp the cannula 12 while engaging the suture tourniquet 30 and clamp 18. Such a configuration minimizes occupancy of the apparatus 10 while maximizing the working space available for a surgeon.

In a preferred embodiment, therefore, a single cannula 12 performs multiple functions, including clamping, perfusion of cardioplegia and oxygenated blood, venting, occlusion of a blood vessel, and securing of sutures. The apparatus 10 is very convenient to use, and is compact, thereby requiring a smaller surgical opening in the patient, which in turn reduces the trauma to the patient.

Various alternative clamps 18 and intraluminal occlusion devices 15 may be used in accordance with the present invention. Unless specified otherwise, the clamp may be made of plastic or stainless steel, or other similar materials. It may also be desirable for the clamp to be malleable, thereby allowing a surgery to preform the clamp before placing the clamp on the blood vessel of the patient, to accommodate the particular size and geometry of the blood vessel. Similarly, the expandable members described below, including balloons and diaphragms, may be made of PET, latex or similar material.

Another embodiment of the present invention is illustrated in FIGS. 4–7. A cannula 12 having perfusion lumen 28, a venting lumen 29, a cardioplegia lumen 76, and a balloon inflation lumen 78, is slidably disposed in shaft 91 which in turn is coupled to a clamp body 40 having a channel with clamps for easy attachment coupling of cannula 12. In a preferred embodiment both clamp body 40 and 91 are malleable, allowing them to be bent or moved out of the way.

Shaft 91 of cannula 12 is configured having a proximal portion comprising a handle 90 which may be configured to be activated by the fingers of the surgeon. Distal movement of the handle 109 causes the distal end of the shaft 91 to penetrate the wall of the vessel. FIG. 7 shows a detailed view of the distal end of shaft 91 comprising a trocar 33, the expandable member 15 being positioned within the distal tip of the trocar, which is further provided with an expandable opening 79 through which the expandable member 15 is discharged. Following penetration of the vessel with the trocar 33, a second handle 111 can be activated with the thumb of the surgeon to deploy the unexpanded expandable member 15 into the lumen of the vessel. Following deployment of the expandable member 15, inflation fluid may be provided through inflation lumen 78 to cause the member 15 to expand and occlude the lumen of the vessel.

The clamp 18 has two jaws 34 movedly coupled to each other to allow the clamp to be opened and closed around an outer periphery of a blood vessel. FIG. 7 shows one configuration of jaws 34 wherein the upper jaw is configured with having a first and second jaw member disposed about the vessel. The lower jaw is configured having only a singly jaw member which is received between the first and second member of the upper jaw when the clamp is in the fully closed position. The clamp is movable between an open position (not shown) and a closed position by actuation of clamp handle 89. If desired, a jaw insert 37 having a selected thickness 38 may be coupled to an inner region of the jaws 34 of clamp 18. In this manner, the inner diameter of the clamp may be adjusted to accommodate different diameter blood vessels. It should further be noted that an inner surface of the clamp and of the insert 37 is shaped to substantially conform to the outer surface 20 of blood vessel 11.

Figure 8A:
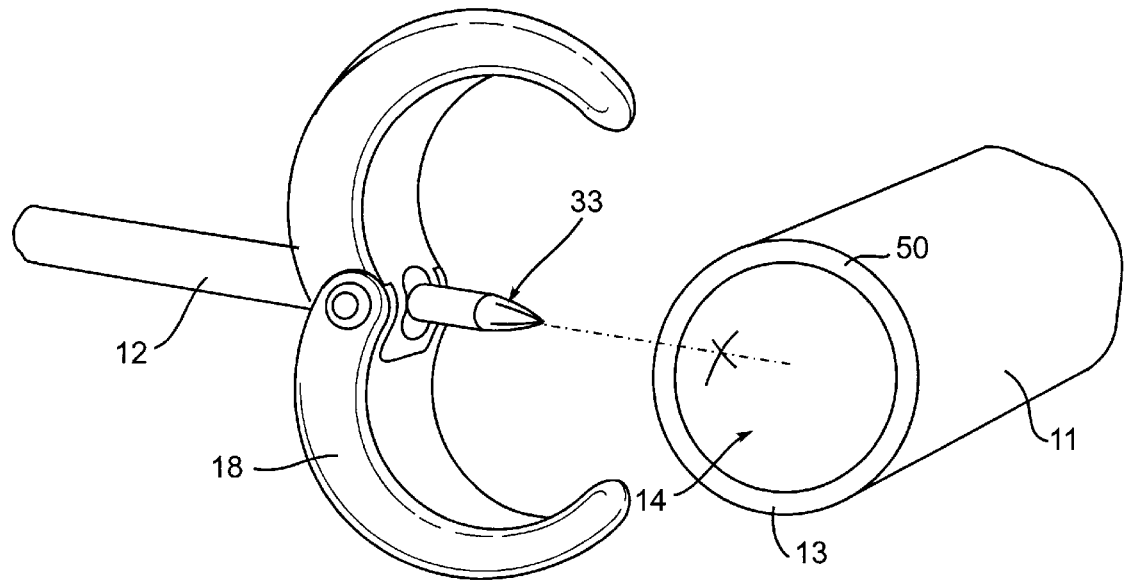
FIG. 8A is an isometric view of an apparatus for occluding a blood vessel provided in accordance with the present invention shown approaching a blood vessel.
Figure 8B:
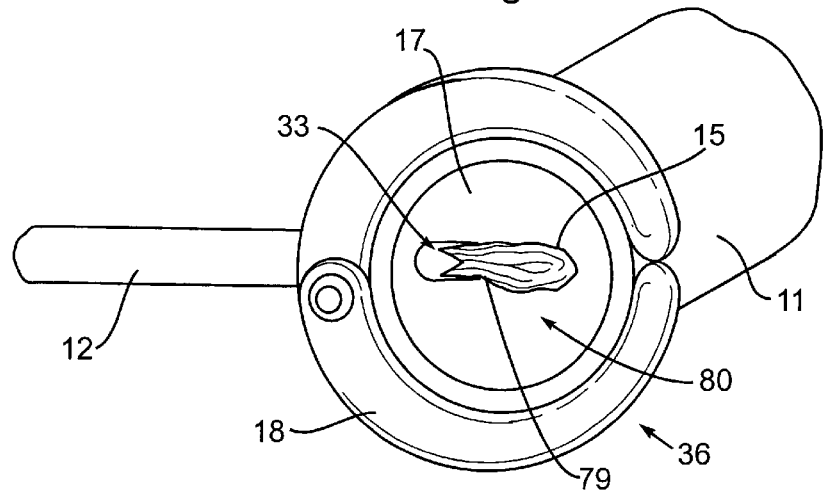
FIG. 8B is an isometric view of the apparatus of FIG. 8A shown engaging the blood vessel.
Figure 8C:
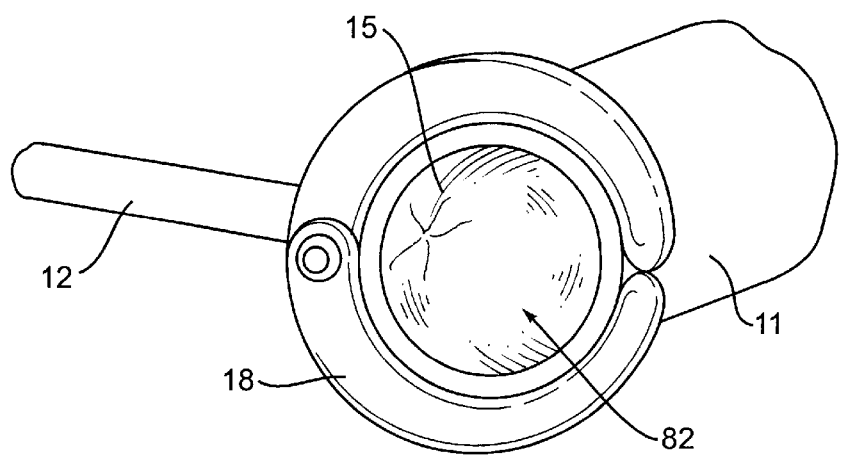
FIG. 8C is an elevational view of the apparatus of FIGS. 8A and B illustrating an expandable member in an expanded condition inside the blood vessel.

Turning now to a description of the embodiment of FIGS. 8A–C, coupled to a distal end of cannula 12 is a trocar 33, the expandable member 15 being positioned within the distal tip of the trocar, which is further provided with an expandable opening 79 through which the expandable member 15 is discharged. The distal end of the trocar 33 may be adapted to puncture through the wall 13 of blood vessel 11, or as illustrated in FIG. 8A, it may be inserted through an incision 50 made in the blood vessel wall. Once the expandable member 15 is discharged into the lumen 14 of the blood vessel in a collapsed position 80, as illustrated in FIG. 8B, the expandable member is inflated to an expanded condition 82, as illustrated in FIG. 8C, by the introduction of liquid, gas or foam.

Figure 9:
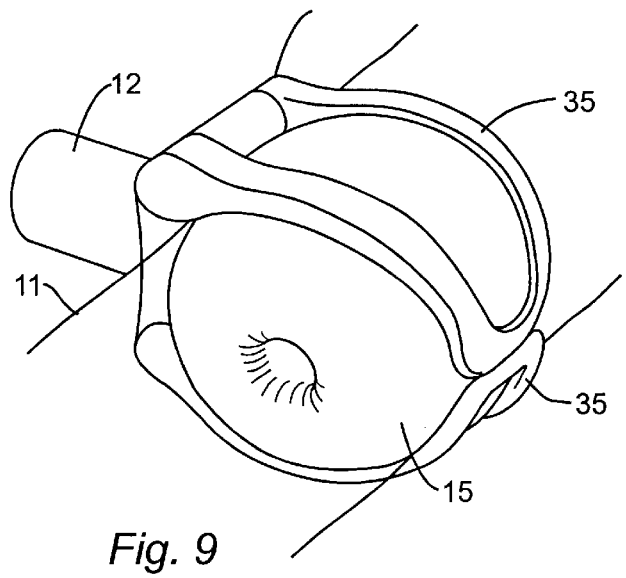
FIG. 9 is a front isometric view an apparatus for occluding a blood vessel provided in accordance with the present invention.
Figure 10:
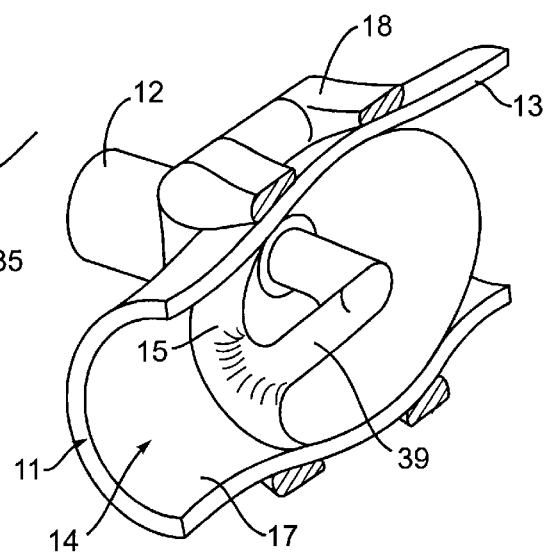
FIG. 10 is a cross-sectional isometric view of the apparatus of FIG. 9.

A number of clamp designs are appropriate for the teachings of the present invention. In addition to those clamp configurations described above, FIG. 8A shows a clamp 18 having a pair of single member arms 35 which are hinged at the distal end of the cannula 12. The arcuate upper and lower arm are closed to confine the vessel 11 therein and the expandable member is deployed as described above. FIG. 9 also shows an alternate configuration of arms 35 wherein the upper and lower arms are configured with a cutout portion to more securely maintain the orientation and position of the clamp 18 on the vessel 11. As further illustrated in FIGS. 9 and 10, the expandable member 15 may further be provided with an integral lumen 39, allowing perfusion of blood or cardioplegia through the cannula 12 and expandable member 15 into the lumen 14 of the blood vessel 11.

Figure 11:
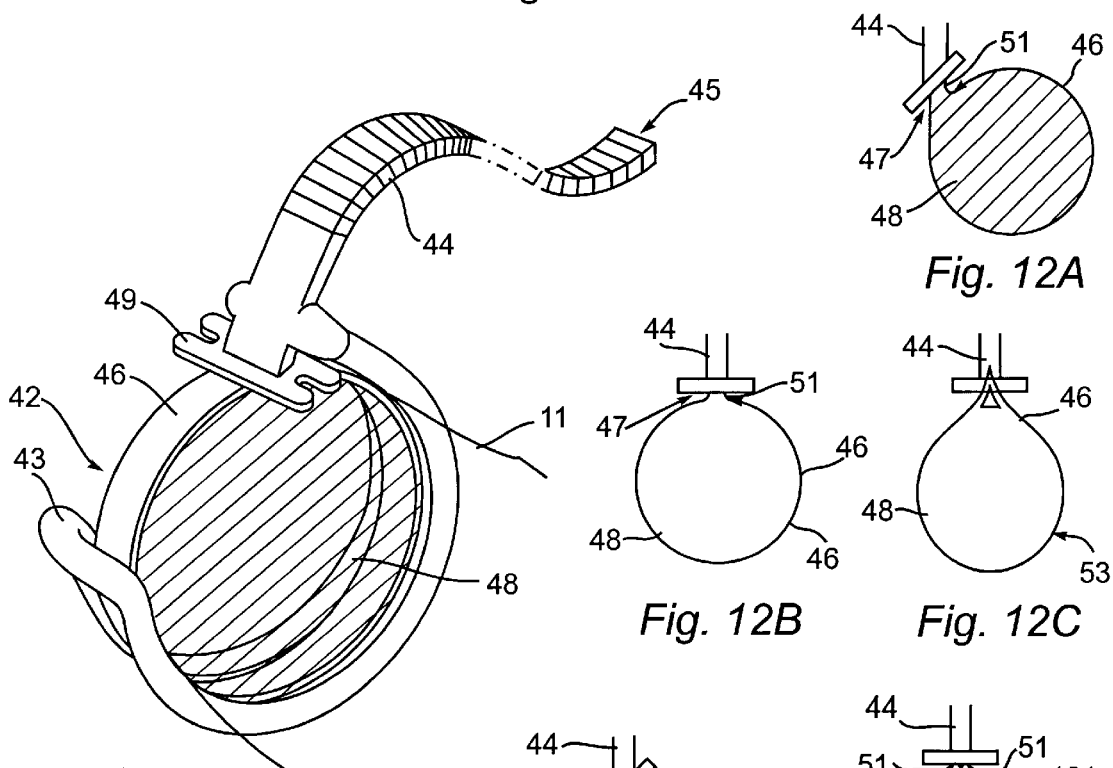
FIG. 11 is an isometric view of an apparatus for occluding a blood vessel provided in accordance with the present invention.

In an alternative embodiment, as illustrated in FIG. 11, the clamp may have a single arm 43 having a substantially "C" shaped cross-section having a more closed configuration than the arcuate arms of previously described configurations. The arm 43 has an open region 42 sufficiently large to allow the clamp to be hooked around the outer surface of blood vessel 11. The clamp 43 is coupled to a semi-rigid sheath 44 which is hollow such that a passageway 45 extends through the length of the sheath 44. When aligned with an incision in the wall of the vessel, an intraluminal occlusion device may be passed through sheath 44 through the incision into the lumen 14 of the vessel.

For example, as illustrated in FIG. 11, a band 46 is slidably disposed within the passageway 45, a distal end 47 of the band 46 being sufficiently flexible and preformed to curve around an inner circumference of the vessel as the band 46 is pushed out of the sheath 44. In a preferred embodiment, an expandable diaphragm 48 is coupled to an end region 49 of sheath 44 such that as the distal end of the band 46 is pushed out of the sheath 44, it engages and expands the expandable diaphragm 48, thereby substantially filling the inner diameter of the lumen of the blood vessel with a tambourine-like member comprised of the band 46 covered by the expandable diaphragm 48. Given the spatial relationship of the sheath and clamp, the band 46 is aligned with the clamp 43 as it expands to fill an inner region of the blood vessel 11. The clamp 43 and intraluminal occlusion device thereby work in combination as described above to occlude the blood vessel and retain the intraluminal occlusion device in a selected location.

Figure 12A:
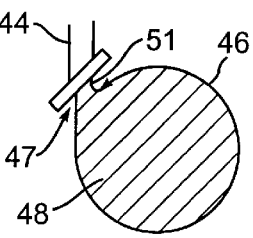
FIGS. 12A–E are schematic illustrations of alternative embodiments of a portion of the apparatus of FIG. 11.
Figure 12B:
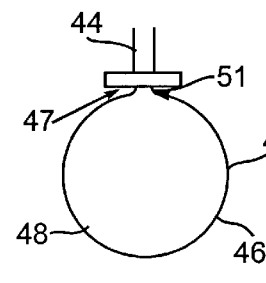
Figure 12C:
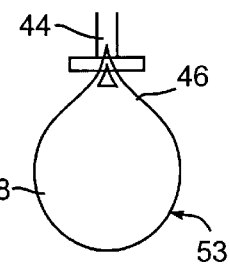
Figure 12D:
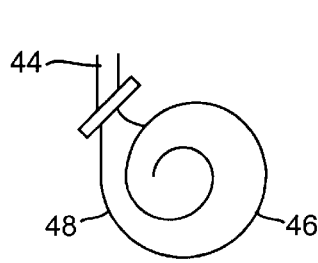
Figure 12E:
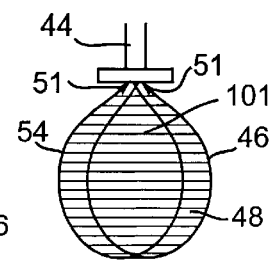

The band 46 may be coupled to the sheath 44 and expand within the blood vessel lumen in a variety of ways. For example, as illustrated in FIG. 12A, the band is connected via a hinge 51 and begins its expansion around an inner circumference of the blood vessel 11 in a direction that is substantially tangential to the inner circumference of the blood vessel. It is believed that this may minimize scraping of the wall and production of emboli. Alternatively, the band 46 may be coupled via a hinge 51 and expand into the lumen of the blood vessel in a direction that is substantially perpendicular to the inner circumference of the blood vessel, as illustrated in FIG. 12B. As illustrated in FIG. 12C, the band 46 may be in the form of a loop 53 that is pushed out of the distal end of sheath 44. In an alternative embodiment, as illustrated in FIG. 12D, the band 46 curls around itself as it is pushed from the sheath 44 to fill a cross-sectional area of the lumen of the blood vessel with an increasing radius curve. Further, as illustrated in FIG. 12E, a second band 54 may be slidably disposed within the passageway 45 of sheath 44 and pushed out of the sheath 44 in combination with the band 46 to define an overlapping portion 101, wherein the first and second bands engage the expandable diaphragm 48 and fill a cross-sectional area of the lumen of the blood vessel.

Figure 13:
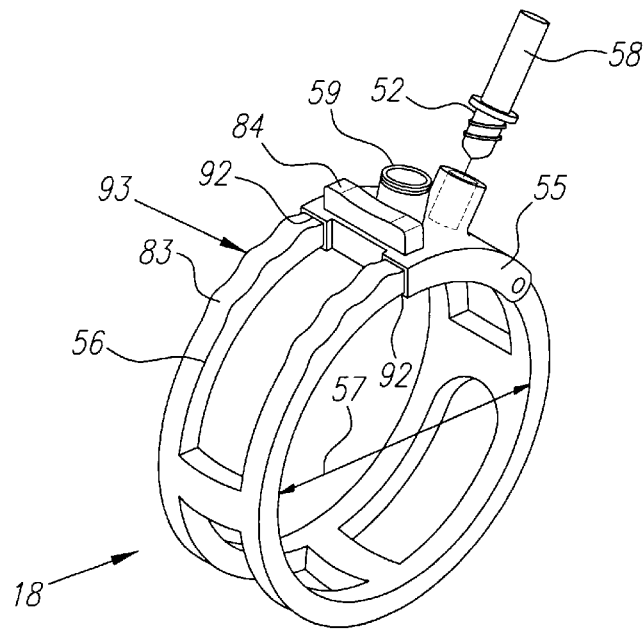
FIG. 13 is a front isometric view of an apparatus for occluding a blood vessel provided in accordance with the present invention.
Figure 14A:
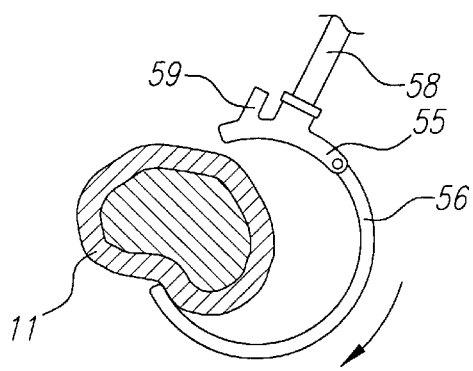
FIGS. 14A–D are schematic illustrations of the apparatus of FIG. 13 shown in use to occlude a blood vessel.

In an alternative embodiment, as illustrated in FIG. 13, the clamp 18 has a first arcuate member 55 hingedly coupled to a second arcuate member 56. When in an open position, as illustrated in FIG. 14A, the clamp 18 is hooked around the blood vessel 11, after which a distal end 93 of arcuate member 56 is inserted into recesses 92 provided in the first arcuate member 55. In a preferred embodiment, the distal end 93 of arcuate member 56 is provided with a plurality of detents or ridges 83 to close the clamp in any one of a plurality of discrete positions having a different inner diameter 57, to thereby accommodate blood vessels of varying outer diameters.

Figure 14B:
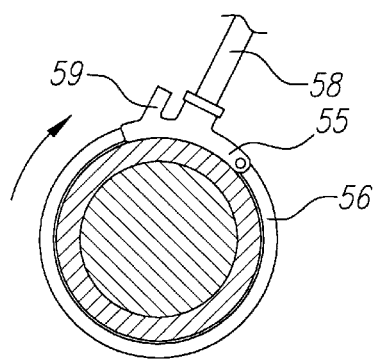
Figure 14C:
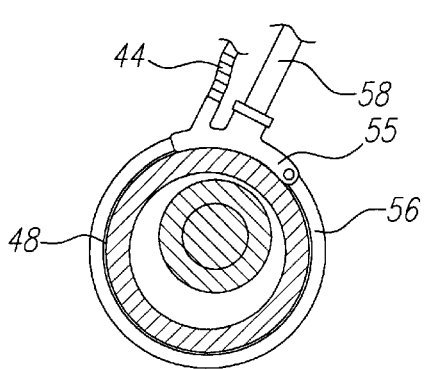
Figure 14D:
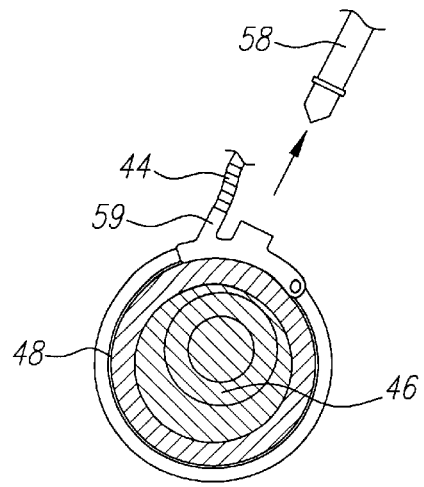

Once the clamp is secured around the blood vessel 11, as illustrated in FIG. 14B, an intraluminal occlusion device, such as that illustrated in FIGS. 11–12, may be inserted through a hollow mount 59 integrally formed in the clamp 18. By aligning the mount 59 with an incision in the wall of the blood vessel, the occlusion device may pass through the clamp into an inner region of the blood vessel, to thereby expand and fill a cross-sectional area of the blood vessel as illustrated in FIGS. 14C and 14D. Alternatively, the occlusion device may include a trocar or other means for piercing the wall of the vessel.

The clamp is further provided with a detachable handle 58, for example, via quick threads 52, to allow the surgeon to quickly and simply remove the handle 58 from the clamp, as illustrated in 14D. The handle 58 may also be malleable, allowing it to remain coupled to the clamp, yet be bent out of the way as necessary. A removable stylet may be provided in a lumen of the malleable handle to give the handle rigidity while the clamp is being positioned. Once the clamp is positioned, the stylet is removed from the lumen of the handle, and the handle is laid out of the way. When it is desired to remove the clamp, a quick release button 84 is depressed, thereby releasing the second arcuate member from engagement with the first arcuate member 55.

In an alternative embodiment as illustrated in FIGS. 15–19, an external clamp 18 comprises a shaft 61 having a band 60 that is slidably disposed along and past a distal end 62 of the shaft 61. The band 60 is sufficiently pliable and preshaped to form a loop around the blood vessel 11 as the distal end of the band 60 is moved past the distal end of the shaft 61. Although this relative movement may be achieved in various of ways, in a preferred embodiment, the shaft 61 is coupled to a handle 85 provided with a knob 86 which is coupled to the band 60, such that movement of the knob 86 downward through the slot 94 of handle 85 causes the band 60 to move past the end of the shaft 61 and loop around the blood vessel 11. In a preferred embodiment, band 60 is made of plastic, Nitenol®, or a stainless steel core covered with rubber or foam, to minimize any trauma to the exterior surface of the blood vessel 11.

Figure 18A:
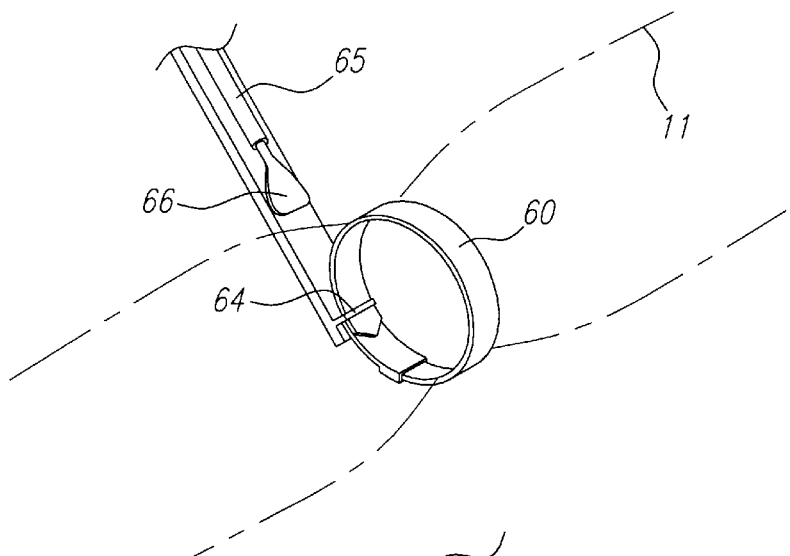
FIG. 18A–B are isometric views of the apparatus of FIG. 15 illustrating an element into alternative positions.
Figure 18B:
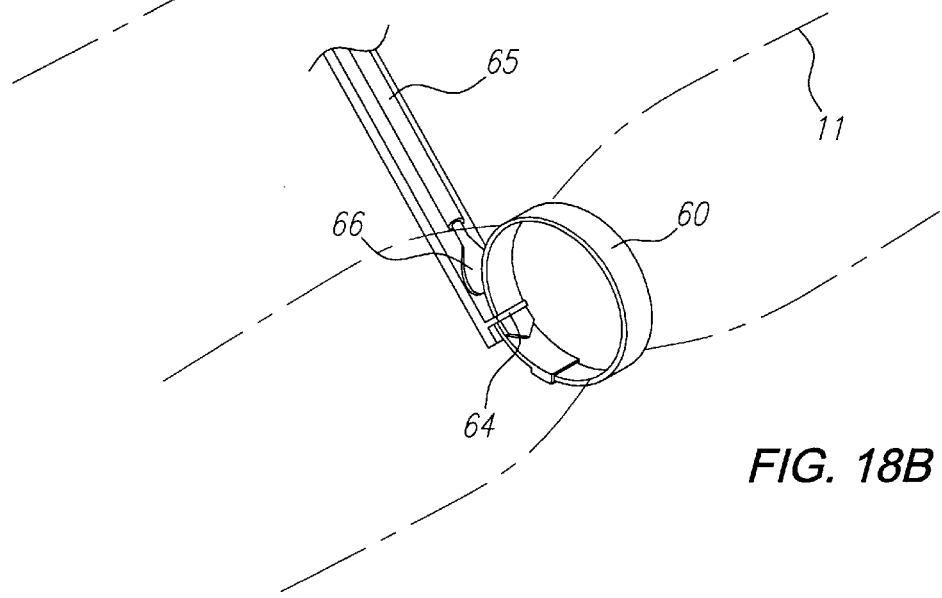
Figure 19:
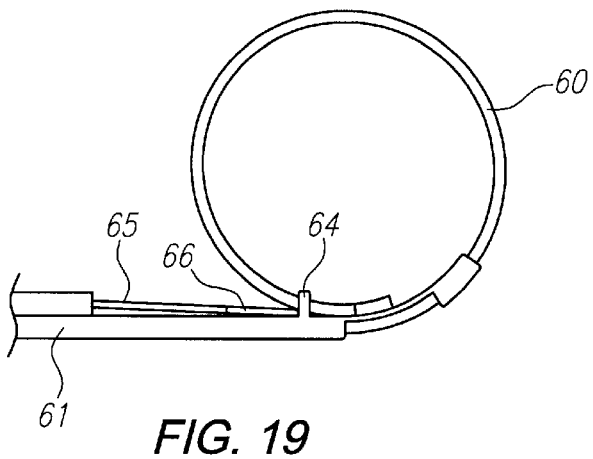
FIG. 19 is a side elevational view of the apparatus of FIG. 15.

The shaft 61 is further provided with a locking member 63 to engage the end of the band 60 and maintain it in a selected position. In a preferred embodiment, the locking member 63 includes a bracket 64 having a sufficient width to receive the distal end of the band. In addition, a rod 65 having a substantially flat distal end 66 is slidably disposed along shaft 61. As best seen in FIGS. 18–19, once the distal end of band 60 is passed through bracket 64, the rod 65 is slid downward, thereby wedging the substantially flat distal end 66 into the bracket 64 between the band 60 and shaft 61 to further secure the band 60 in a selected position around the blood vessel.

Figure 20:
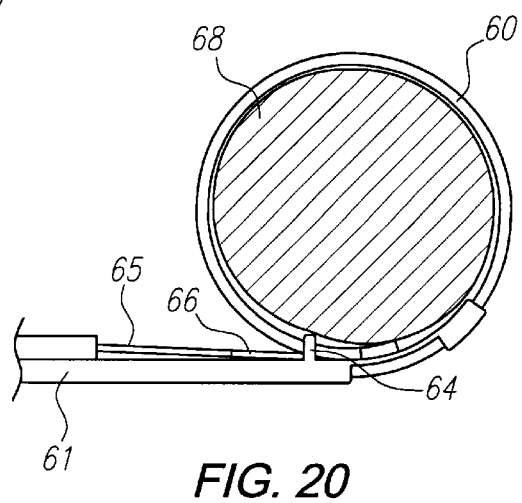
FIG. 20 is a side elevational view of the apparatus of FIG. 19 shown in use to occlude a blood vessel.

Although the clamp illustrated in FIGS. 15–20 may be used with a variety of intraluminal occlusion devices, in a preferred embodiment, as illustrated in FIG. 20, a second band 67 is slidably disposed on the shaft 61. The second band 67 is adapted to be inserted through the wall of the blood vessel, and is sufficiently pliable and preshaped to form a loop around an inner lumen of the blood vessel as the second band 67 is moved past the distal end of the shaft 61. An expandable diaphragm 68 is coupled to the distal end of the second band, such that as the second band 67 expands within the lumen of the blood vessel, it causes the expandable diaphragm to expand, thereby filling a cross-sectional area of the lumen of the blood vessel. The band 60 and second band 67 are aligned such that they follow a similar track around the circumference of the blood vessel, but on opposite sides of the vessel wall. Therefore, as the second band 67 expands within the vessel lumen, the outer band 60 is tightened about the exterior of the vessel 11 so that the vessel is occluded while maintaining the position and orientation of the clamp 18. The expandable diaphragm 68 is preferably configured from rubber, silicon, or other flexible elastic, impermeable material.

Figure 21:
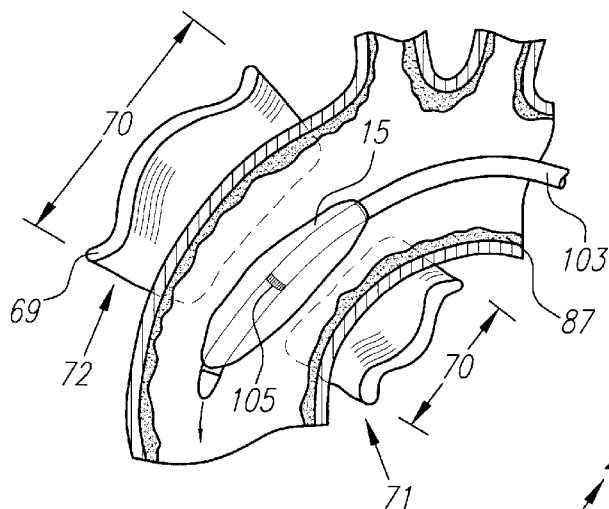
FIG. 21 is a cross-sectional elevational view of an apparatus for occluding a blood vessel provided in accordance with the present invention.
Figure 22:
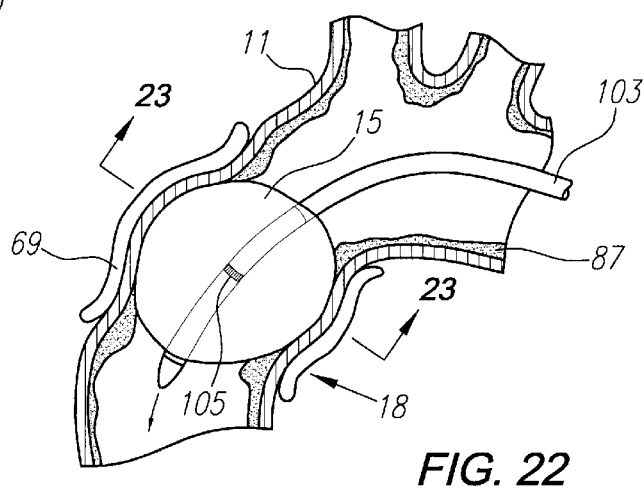
FIG. 22 is a cross-sectional elevational view of the apparatus of FIG. 21 shown in engagement with a blood vessel.
Figure 23:
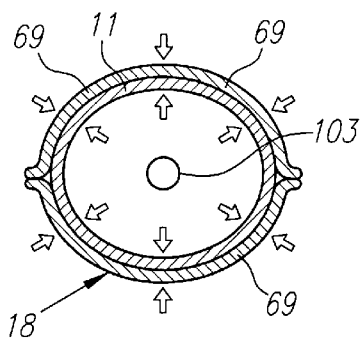
FIG. 23 is a cross-sectional elevational view taken along line 23–23 of FIG. 22.

In an alternative embodiment as illustrated in FIGS. 21–23, the clamp has a substantially "S" shaped cross-section which is disposed about the circumference of the aorta as seen in FIG. 23. The clamp is designed to fit around the wall of the aorta at the location occluded by cannula 103 having an expandable member 15 disposed thereon. In use, the cannula 103 may be inserted transaortically or endovascularly into the aorta of the patient. The clamp is secured in the region of interest and the expandable member is expanded using inflation fluid provided to the member 15 through inflation port 105. The cannula 103 may be provided with internal lumens which can be used to provide cardioplegia, arterial perfusion, venting or other functions within the vessel lumen.

The width 70 of the clamp is smaller at a first end 71 as compared to a second end 72. As illustrated in FIG. 23, a clamp having the illustrated configuration puts very little pressure on the vessel wall, but rather contains the expandable member 15 to achieve an occluding seal, without needing to overexpand the expandable member 15 and risk dissection and trauma to the walls of the vessel.

Figure 24:
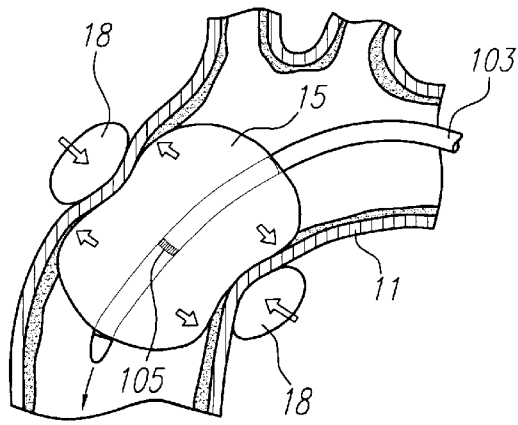
FIG. 24 is a cross-sectional elevational view of an apparatus for occluding a blood vessel provided in accordance with the present invention.
Figure 25:
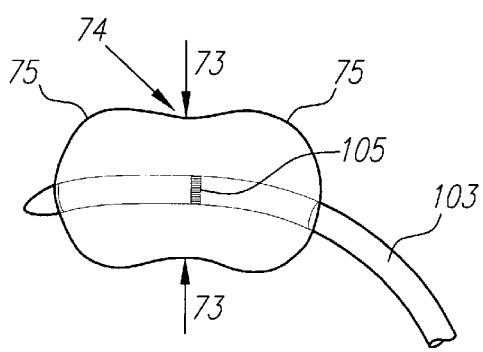
FIG. 25 is a side elevational view of an element of the apparatus illustrated in FIG. 24.

As illustrated in FIGS. 24 and 25, the expandable member 15 may have an outer diameter 73 that is smaller in a central region 74 than in and end region 75 on either side of the central region. Such a configuration increases the surface contact and secureness of the position of the inflatable member within the lumen.

Figures 26A, 26B, 26C, 26D:
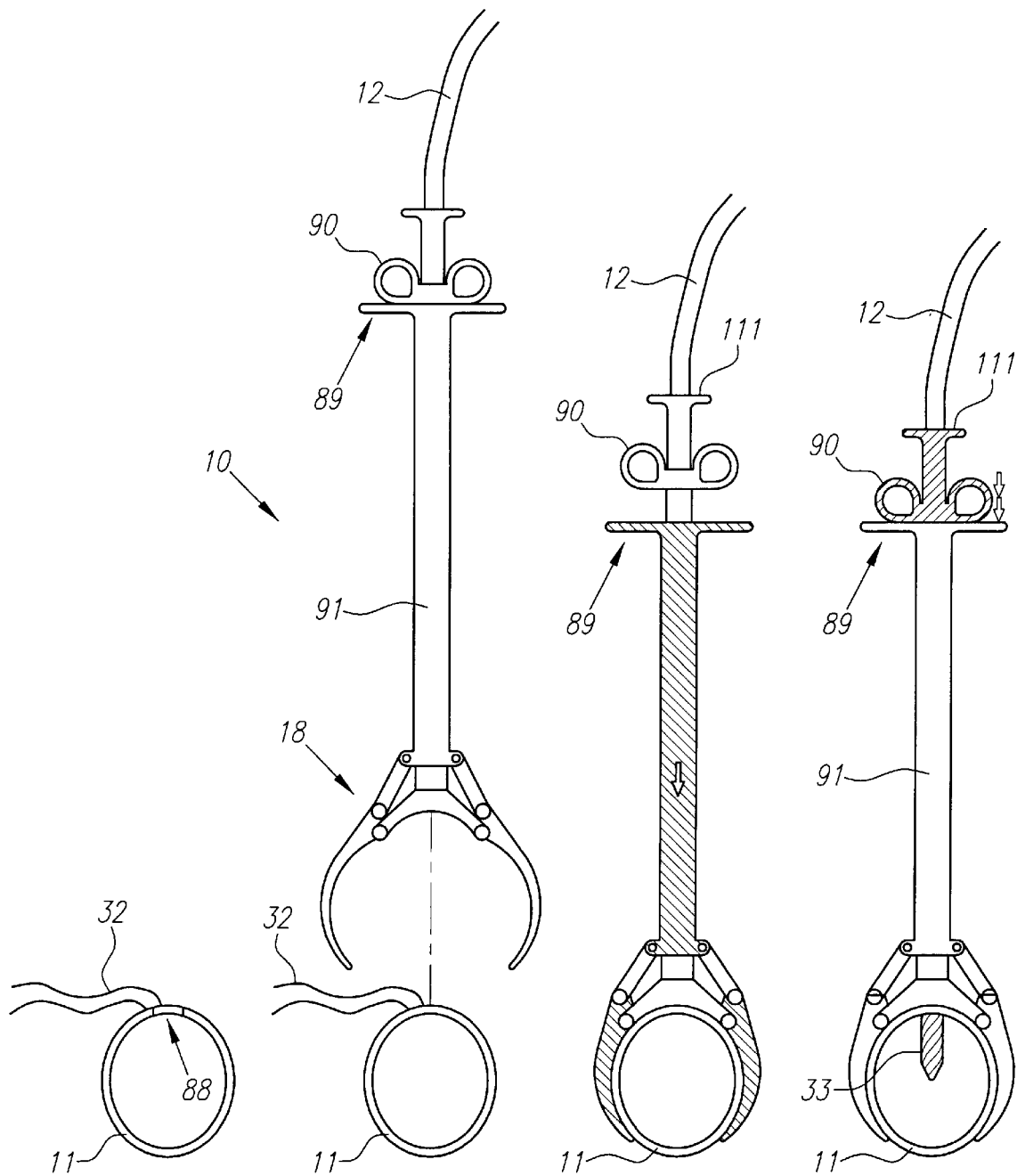

Illustrated in FIG. 26 is one preferred method by which a blood vessel 11 may be occluded in accordance with the present invention by providing a clamping device 10 having a clamp 18 coupled to a distal end of a malleable shaft 91. After a purse string suture 32 is made in the vessel 11 at a selected location 88 as illustrated in FIG. 26A, the apparatus 10 is moved toward the blood vessel 11 with the clamp 18 in an open position, as illustrated in FIG. 26B. The clamp 18 is closed around the outer periphery of the blood vessel thereby substantially engaging an outer periphery of the blood vessel at the selected location 88, as illustrated in FIG. 26C.

Although closing of the clamp may be accomplished in a variety of ways, in the embodiment illustrated in FIG. 26, a clamp handle 89 is slid downward causing the jaws of the clamp 18 to close about the vessel 11. Once the clamp is secured about the vessel, cannula handle 90 is advanced distally to cause trocar 33 to pierce the wall of the vessel 11 as shown in FIG. 26D. The cannula 12 includes an expandable member 15 coupled to a distal end, as described previously with respect to FIGS. 1–8. The cannula is slidably disposed within a trocar 33 coupled to trocar handle 90, which in turn is slidably disposed within a lumen of shaft 91. As illustrated in FIG. 26E, the distal end of the cannula 12 carrying the inflatable member 15 is deployed through an expandable opening in the tip of the trocar 33 as the trocar is removed upward by pulling on trocar handle 90 and pushing distally on the second handle 111.

The expandable member is expanded following deployment to engage an inner wall of the blood vessel 11 at the selected region, aligned with clamp 18, the clamp and the inflatable member thereby working in cooperation to occlude the blood vessel. Pliable handle or shaft 91 may then be laid out of the way while a surgical procedure, such as a stopped-heart cardiac surgical procedure, is performed. Once the surgical procedure is completed, the expandable member is deflated, the clamp assembly is removed, and the purse string suture 32 is tightened.

An improved apparatus for occluding a blood vessel has been shown and described. From the foregoing, it will be appreciated that although embodiments of the invention have been described herein for purposes of illustration, various modifications may be made without deviating from the spirit of the invention. Thus, the present invention is not limited to the embodiments described herein but rather is defined by the claims which follow.

What is claimed is:

1. An apparatus for occluding a blood vessel comprising:

a cannula adapted for insertion through a wall of a blood vessels, said cannula having a first lumen having a proximal opening and a distal opening;

an expandable member coupled to a distal end of the cannula, the expandable member having an integral lumen formed therethrough, said integral lumen being fluidly coupled to said distal opening of the cannula and having at least one opening on the exterior of the expandable member the expandable member having a sufficient size when expanded to be adjacent an inner surface of the lumen of the blood vessel; and a clamp coupled to the cannula, the clamp having an inner surface configured to engage an outer surface of an annular region of the blood vessel and being aligned with the expandable member such that the clamp moves the annular region of the blood vessel into contact with the expandable member to occlude the blood vessel and maintain the expandable member in a desired location.

2. The apparatus according to claim 1 wherein the proximal opening of the first lumen is coupled to a source of oxygenated blood to perfuse the blood vessel through said at least one opening on the exterior of the expandable member.

3. The apparatus according to claim 1 wherein the distal end of the cannula is provided with a second opening in fluid communication with a second lumen extending through the cannula to allow fluid to flow through the cannula into the blood vessel.

4. The apparatus according to claim 3 wherein the second lumen is coupled to a source of cardioplegia.

5. The apparatus according to claim 1 wherein the distal end of the cannula is provided with a third opening in fluid communication with a third lumen extending through the cannula to allow fluid to flow out from the blood vessel through the cannula.

6. The apparatus according to claim 5 wherein the third lumen is coupled to a vacuum source.

7. The apparatus of claim 1 wherein the expandable member is contained within a trocar coupled to the distal end of the cannula, the trocar being adapted to penetrate the wall of the blood vessel.

8. The apparatus according to claim 7 wherein the clamp has two jaws that are hingedly coupled to each other to move between an open position and a closed position, an inner surface of the jaws being concave to substantially conform to the outer surface of the blood vessel.

9. Apparatus for occluding a blood vessel comprising:

an intraluminal occlusion device that is expandable to a size wherein the intraluminal occlusion device is adjacent an inner surface of a blood vessel; and a clamp having a first arm and a second arm, the first and second arms having fixed interior surfaces adapted to substantially conform to and engage an outer surface of an annular region of the blood vessel when the first and second arms are closed relative to one another, the clamp being aligned with the intraluminal occlusion device such that the fixed interior surfaces of the first and second arms move the annular region of the blood vessel into contact with the intraluminal occlusion device, the intraluminal occlusion device and the clamp thereby working in cooperation to occlude the blood vessel and maintain the intraluminal occlusion device in a desired location.

10. The apparatus according to claim 9 wherein the first arm and the second arm are arcuate-shaped and the first arm is hingedly coupled to the second arm.

11. The apparatus according to claim 10 wherein the clamp is provided with an integral hollow mount through which the intraluminal occlusion device may be passed to extend through the clamp and through an incision in a wall of the blood vessel.

12. The apparatus according to claim 9 wherein at least one of the first arm and the second arm has a central cutout portion substantially aligned with the center of the intraluminal occlusion device.

13. A method of temporarily occluding a blood vessel comprising the steps of:

providing a clamping device having a semi-rigid shaft, the semi-rigid shaft having a clamp on a distal end thereof and a lumen extending between a proximal end and the distal end of the shaft;

providing a catheter having an expandable member coupled to a distal end thereof;

providing a trocar slidably disposed over the catheter, wherein the trocar has a distal tip with an expandable opening;

creating a purse string suture at a selected location at a selected region of the blood vessel;

directing the distal end of the clamping device to the selected region with the clamp in an open position;

closing the clamp around the blood vessel, thereby substantially engaging an outer periphery of the blood vessel at the selected region;

inserting the catheter and the trocar through the lumen in the clamping device;

extending the distal tip of the trocar through the wall of the blood vessel at the selected region;

deploying the distal end of the catheter and the expandable member coupled thereto through the expandable opening in the trocar;

expanding the expandable member to engage an inner wall of the blood vessel at the selected regions;

performing a surgical procedure while the expandable member is expanded;

deflating the expandable member; and withdrawing the catheter with the expandable member coupled thereto from said vessel.

14. The method according to claim 13 wherein said surgical procedure is a stopped-heart cardiac procedure.

15. The apparatus according to claim 13 wherein the distal tip of the trocar is adapted to puncture the wall of the blood vessel.

16. The apparatus according to claim 13 further including the step of creating an incision through the vessel wall at the selected location and wherein said distal tip of said trocar is adapted to be inserted through the incision.

* * * * *